(12) United States Patent
Pruski et al.

(10) Patent No.: US 12,085,035 B2
(45) Date of Patent: Sep. 10, 2024

(54) METHOD AND SYSTEM FOR EVALUATING A NOx SENSOR

(71) Applicant: GM GLOBAL TECHNOLOGY OPERATIONS LLC, Detroit, MI (US)

(72) Inventors: Erika L. Pruski, Brighton, MI (US); Janean E. Potter, Northville, MI (US); Rafat F. Hattar, Royal Oak, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 17/987,163

(22) Filed: Nov. 15, 2022

(65) Prior Publication Data

US 2024/0159197 A1   May 16, 2024

(51) Int. Cl.
  *F01N 11/00*   (2006.01)
  *F02D 41/14*   (2006.01)
  *G01N 33/00*   (2006.01)

(52) U.S. Cl.
  CPC ........ *F02D 41/1463* (2013.01); *F01N 11/002* (2013.01); *G01N 33/0063* (2013.01); *G01N 33/007* (2013.01); *F01N 2560/026* (2013.01); *F01N 2900/1402* (2013.01); *G01N 33/0037* (2013.01)

(58) Field of Classification Search
  CPC .............. F02D 41/1463; F01N 11/002; F01N 2560/026; F01N 2900/1402; G01N 33/0063; G01N 33/007; G01N 33/0037
  See application file for complete search history.

(56) References Cited

U.S. PATENT DOCUMENTS

| | | | |
|---|---|---|---|
| 10,859,018 B1* | 12/2020 | Lee | F01N 3/101 |
| 2010/0024389 A1* | 2/2010 | Gady | B01D 53/9409 |
| | | | 60/274 |
| 2010/0218487 A1* | 9/2010 | Wang | F01N 11/007 |
| | | | 60/287 |
| 2011/0192144 A1* | 8/2011 | Yasui | F02D 41/1475 |
| | | | 60/276 |
| 2014/0298777 A1* | 10/2014 | Koga | F02D 41/1462 |
| | | | 60/274 |
| 2014/0360166 A1* | 12/2014 | Chandrasekaran | F02D 41/222 |
| | | | 60/274 |
| 2019/0292970 A1* | 9/2019 | Ikedo | F01N 3/101 |
| 2022/0127995 A1* | 4/2022 | Cavataio | F01N 3/208 |

FOREIGN PATENT DOCUMENTS

CN 112730568 A * 4/2021 .......... G01N 27/406

* cited by examiner

*Primary Examiner* — Matthew T Largi
(74) *Attorney, Agent, or Firm* — Quinn IP Law (57) ABSTRACT

The concepts described herein relate to a system, method, and/or apparatus for monitoring a NOx sensor that is arranged in an exhaust gas feedstream of an internal combustion engine downstream of an exhaust aftertreatment system to detect a fault related to the NOx sensor. This includes utilizing a catalyst efficiency model to detect occurrence of a fault that may indicate an in-range biased or stuck NOx sensor.

15 Claims, 3 Drawing Sheets

METHOD AND SYSTEM FOR EVALUATING A NOx SENSOR

INTRODUCTION

Internal combustion engines may employ an exhaust gas emissions system that includes a tail-pipe sensing system capable of monitoring nitrogen oxides in the exhaust gas feedstream for purposes of engine control, monitoring, and fault detection and diagnostics.

SUMMARY

The concepts described herein relate to a system, method, and/or apparatus for monitoring a NOx sensor that is arranged in an exhaust gas feedstream of an internal combustion engine downstream of an exhaust aftertreatment system to detect a fault related to the NOx sensor. This includes utilizing a catalyst efficiency model to detect occurrence of a fault that may indicate an in-range biased or stuck NOx sensor.

An aspect of the disclosure may include determining a temperature of an exhaust purifying device of the exhaust aftertreatment system; determining an exhaust gas flowrate; determining an air/fuel ratio of the exhaust gas feedstream; determining an oxygen storage capacity of the exhaust purifying device; and determining an efficiency of the exhaust purifying device based upon the oxygen storage capacity; determining an expected NOx concentration in the exhaust gas feedstream based upon the air/fuel ratio of the exhaust gas feedstream, the efficiency of the exhaust purifying device, and the exhaust gas flowrate, and determining a measured NOx concentration in the exhaust gas feedstream based upon a signal input from the NOx sensor. The measured NOx concentration in the exhaust gas feedstream is compared with the expected NOx concentration in the exhaust gas feedstream to detect a fault in the NOx sensor.

Another aspect of the disclosure may include detecting the fault related to the NOx sensor when an absolute difference between the measured NOx concentration in the exhaust gas feedstream and the expected NOx concentration in the exhaust gas feedstream is greater than a threshold.

Another aspect of the disclosure may include detecting a biased-high sensor offset fault when the air/fuel ratio is stoichiometric or rich and the absolute difference between the measured NOx concentration in the exhaust gas feedstream and the expected NOx concentration in the exhaust gas feedstream is greater than the threshold.

Another aspect of the disclosure may include detecting a biased-low sensor offset fault when the air/fuel ratio is lean and the absolute difference between the measured NOx concentration in the exhaust gas feedstream and the expected NOx concentration in the exhaust gas feedstream is greater than the threshold.

Another aspect of the disclosure may include detecting a stuck-in-range sensor fault when the air/fuel ratio is transitioning between a lean air/fuel ratio and a rich air/fuel ratio and the absolute difference between the measured NOx concentration in the exhaust gas feedstream and the expected NOx concentration in the exhaust gas feedstream is greater than the threshold.

Another aspect of the disclosure may include comparing the measured NOx concentration in the exhaust gas feedstream and the expected NOx concentration in the exhaust gas feedstream only when the temperature of the exhaust purifying device indicates the exhaust purifying device has achieved a light-off state.

Another aspect of the disclosure may include comparing the measured NOx concentration in the exhaust gas feedstream and the expected NOx concentration in the exhaust gas feedstream only when the exhaust gas flowrate and the air/fuel ratio of the exhaust gas feedstream determine the expected NOx concentration in the exhaust gas feedstream is accurate.

Another aspect of the disclosure may include determining a temperature of the exhaust purifying device; monitoring, via an upstream exhaust gas sensor and a downstream exhaust gas sensor, the exhaust purifying device; determining an oxygen storage capacity of the exhaust purifying device based upon the temperature of the exhaust purifying device and the monitoring of the exhaust purifying device via the upstream exhaust gas sensor and the downstream exhaust gas sensor; determining an efficiency of the exhaust purifying device based upon the oxygen storage capacity; determining an exhaust gas flowrate; determining an air/fuel ratio of the exhaust gas feedstream; and determining the expected NOx concentration in the exhaust gas feedstream based upon the air/fuel ratio of the exhaust gas feedstream, the efficiency of the exhaust purifying device, and the exhaust gas flowrate.

Another aspect of the disclosure may include a system for monitoring a NOx sensor arranged in an exhaust gas feedstream of an internal combustion engine and downstream of an exhaust purifying device that includes a mass airflow sensor; a first exhaust gas sensor arranged upstream of the exhaust purifying device; a second exhaust gas sensor arranged downstream of the exhaust purifying device; and a controller that is in communication with the mass airflow sensor and the first and second exhaust gas sensors. The controller includes algorithmic code that is executable to determine a temperature of the exhaust purifying device, determine an exhaust gas flowrate, determine an air/fuel ratio of the exhaust gas feedstream, determine an oxygen storage capacity of the exhaust purifying device based upon the temperature of the exhaust purifying device, determine an efficiency of the exhaust purifying device based upon the oxygen storage capacity, determine an expected NOx concentration in the exhaust gas feedstream based upon the air/fuel ratio of the exhaust gas feedstream, the efficiency of the exhaust purifying device, and the exhaust gas flowrate, determine a measured NOx concentration in the exhaust gas feedstream based upon the NOx sensor, compare the measured NOx concentration in the exhaust gas feedstream and the expected NOx concentration in the exhaust gas feedstream, and detect, via the controller, an in-range fault in the NOx sensor when an absolute difference between the measured NOx concentration in the exhaust gas feedstream and the expected NOx concentration in the exhaust gas feedstream is greater than a threshold.

The above summary is not intended to represent every possible embodiment or every aspect of the present disclosure. Rather, the foregoing summary is intended to exemplify some of the novel aspects and features disclosed herein. The above features and advantages, and other features and advantages of the present disclosure, will be readily apparent from the following detailed description of representative embodiments and modes for carrying out the present disclosure when taken in connection with the accompanying drawings and the claims.

BRIEF DESCRIPTION OF THE DRAWINGS

One or more embodiments will now be described, by way of example, with reference to the accompanying drawings, in which.

The appended drawings are not necessarily to scale, and may present a somewhat simplified representation of various features of the present disclosure as disclosed herein, including, for example, specific dimensions, orientations, locations, and shapes. Details associated with such features will be determined in part by the particular intended application and use environment.

DETAILED DESCRIPTION

The components of the disclosed embodiments, as described and illustrated herein, may be arranged and designed in a variety of different configurations. Thus, the following detailed description is not intended to limit the scope of the disclosure, as claimed, but is merely representative of possible embodiments thereof. In addition, while numerous specific details are set forth in the following description in order to provide a thorough understanding of the embodiments disclosed herein, some embodiments can be practiced without some of these details. Moreover, for the purpose of clarity, certain technical material that is understood in the related art has not been described in detail in order to avoid unnecessarily obscuring the disclosure.

For purposes of convenience and clarity only, directional terms such as top, bottom, left, right, up, over, above, below, beneath, rear, and front, may be used with respect to the drawings. These and similar directional terms are not to be construed to limit the scope of the disclosure. Furthermore, the disclosure, as illustrated and described herein, may be practiced in the absence of an element that is not specifically disclosed herein.

As used herein, the term "system" may refer to one of or a combination of mechanical and electrical actuators, sensors, controllers, application-specific integrated circuits (ASIC), combinatorial logic circuits, software, firmware, and/or other components that are arranged to provide the described functionality.

Embodiments may be described herein in terms of functional and/or logical block components and various processing steps. Such block components may be realized by any number, combination or collection of mechanical and electrical hardware, software, and/or firmware components configured to perform the specified functions. For example, an embodiment may employ various combinations of mechanical components and electrical components, integrated circuit components, memory elements, digital signal processing elements, logic elements, look-up tables, or the like, which may carry out a variety of functions under the control of one or more microprocessors or other control devices. In addition, those skilled in the art will appreciate that the embodiments may be practiced in conjunction with mechanical and/or electronic systems, and that the vehicle systems described herein are merely embodiments of possible implementations.

For the sake of brevity, some components and techniques and other functional aspects of the systems (and the individual operating components of the systems) may not be described in detail herein. Furthermore, the connecting lines shown in the various figures contained herein are intended to represent example functional relationships and/or physical couplings between the various elements. Many alternative or additional functional relationships or physical connections may be present in an embodiment of the disclosure.

As employed herein, the term "upstream" and related terms refer to elements that are towards an origination of a flow stream relative to an indicated location, and the term "downstream" and related terms refer to elements that are away from an origination of a flow stream relative to an indicated location.

The use of ordinals such as first, second and third does not necessarily imply a ranked sense of order, but rather may distinguish between multiple instances of an act or structure.

Figure 1:
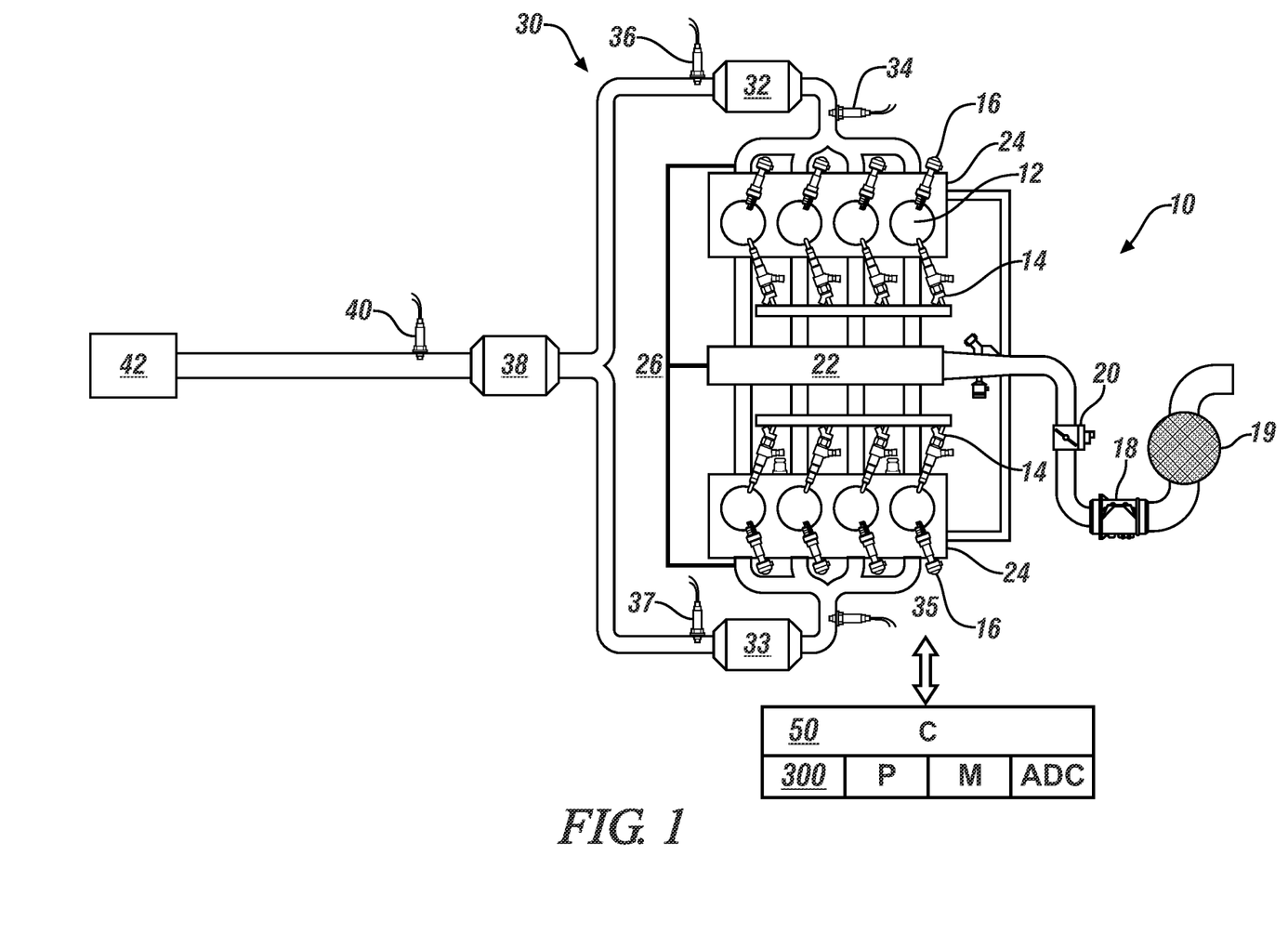
FIG. 1 schematically illustrates an internal combustion engine and exhaust aftertreatment system, in accordance with the disclosure.

Referring to the drawings, wherein like reference numerals correspond to like or similar components throughout the several Figures, FIG. 1, consistent with embodiments disclosed herein, schematically illustrates an internal combustion engine (engine) 10 and associated exhaust aftertreatment system 30 that may be disposed to provide propulsion power to a vehicle. The vehicle may include, but not be limited to a mobile platform in the form of a commercial vehicle, industrial vehicle, agricultural vehicle, passenger vehicle, aircraft, watercraft, train, all-terrain vehicle, personal movement apparatus, robot and the like to accomplish the purposes of this disclosure.

The engine 10 preferably includes a multi-cylinder engine block that define a plurality of cylinders 12 that incorporate movable, reciprocating pistons. An intake manifold 22 is arranged to channel intake air to the plurality of cylinders 12, and an exhaust manifold 24 entrains exhaust gas for channeling through the exhaust aftertreatment system 30.

The engine 10 includes a plurality of direct-injection fuel injectors 14 that are arranged to directly inject fuel into individual combustion chambers associated with the plurality of cylinders 12. The injectors 14 may be a direct-injection device, such as solenoid-activated devices in one embodiment.

The engine 10 includes a plurality of spark ignitors 16 that are arranged to ignite fuel in the individual combustion chambers associated with the plurality of cylinders 12.

The engine 10 also includes an intake air system, which may include an intake air filter 19, a mass air flow (MAF) sensor 18, a throttle valve 20, and other devices and sensors as may be useful.

The engine 10 may include an exhaust gas recirculation (EGR) system 26 that fluidly channels exhaust gas from the exhaust manifold 24 to the intake manifold 22. In one embodiment, the EGR system may include an EGR valve, an EGR cooler including a bypass valve, an EGR outlet temperature sensor, an EGR cooler inlet temperature sensor and a vacuum switch.

Other engine monitoring sensors may include a crankshaft position sensor, a camshaft position sensor, a coolant temperature sensor, an oil level switch, an oil pressure switch, a throttle position sensor, an EGR flow/position sensor, and an intake air temperature sensor, among others. One or more engine monitoring sensors may be replaced with a suitable executable model.

In one embodiment, the engine 10 may include a turbocharger or a supercharger for generating intake air boost pressure, and related sensing devices as may be useful. In one embodiment, this may include a variable geometry turbocharger (VGT) having a turbine that fluidly couples to the exhaust manifold 24 upstream of the exhaust aftertreatment system 30.

Other unillustrated engine components and systems include pistons, crankshaft, engine head(s), intake valves, exhaust valves, camshaft(s), and variable cam phasers when employed.

The engine 10 preferably operates in a four-stroke combustion cycle of repetitively-executed strokes of intake-compression-combustion-exhaust.

Controller 50 monitors various sensing devices and executes control routines to command various actuators to control operation of the engine 10 in response to operator commands. Operator commands may be determined from various operator input devices, including, e.g., a pedal assembly that includes, by way of example, an accelerator pedal and a brake pedal. Other sensing devices associated with engine operation may include, by way of non-limiting example, a barometric pressure sensor, an ambient air temperature sensor, a VGT position sensor (on systems employing a turbocharger), the exhaust gas temperature sensor, an air charge inlet temperature sensor and an air charge outlet temperature sensor, among others.

The exhaust aftertreatment system 30 includes a plurality of fluidly connected exhaust purifying devices for purifying engine exhaust gas prior to expulsion to ambient air through a tailpipe 42. An exhaust purifying device may be a device that is configured to oxidize, reduce, filter and/or otherwise treat constituents of the exhaust gas feedstream, including but not limited to hydrocarbons, carbon monoxide, nitrides of oxygen (NOx), and particulate matter. In the embodiment shown, first, second and third exhaust purifying devices 32, 33, and 38, respectively, are deployed. The first and second exhaust purifying devices 32, 33 may be closely coupled to the exhaust manifold 24, i.e., located within an engine compartment. The third exhaust purifying device 38 may be distally located, such as in an underfloor location when employed on a ground vehicle. The first and second exhaust purifying devices 32, 33 may be oxidation catalysts for oxidizing hydrocarbons and other constituents in the exhaust gas feedstream in certain embodiments. The third exhaust purifying device 38 may include one or more of a three-way oxidation/reduction catalyst, a selective catalyst reduction catalyst (SCR), and/or a particulate filter. A reductant delivery system (not shown) including a reductant injector having an injection nozzle may be positioned upstream relative thereto to controllably supply a reductant into the exhaust gas feedstream to facilitate NOx reduction.

Each of the first, second and third exhaust purifying devices 32, 33, and 38 includes a ceramic or metallic substrate having flow channels that have been coated with catalysis-enhancing materials including, by way of non-limiting examples: platinum-group metals such as platinum, palladium and/or rhodium; other metals, such as copper; cerium; and other materials. The coated materials effect chemical reactions to oxidize, reduce, filter or otherwise treat constituents of the exhaust gas feedstream under certain conditions related to temperature, flowrate, air/fuel ratio and others. The embodiment shown includes the elements of the exhaust aftertreatment system 30 in one arrangement, which is illustrative. Other arrangements of the elements of the exhaust aftertreatment system 30 may be employed within the scope of this disclosure, with such arrangements including addition of other exhaust purifying devices and/or omission of one or more of the exhaust purifying devices, depending upon requirements of the specific application.

Sensors for controlling the engine 10 and monitoring the exhaust purifying devices of the exhaust aftertreatment system 30 may include first and second engine-out exhaust gas sensors 34, 35, respectively, first and second catalyst monitoring exhaust gas sensors 36, 37, and a NOx sensor 40. The first and second engine-out exhaust gas sensors 34, 35, respectively, are arranged in the exhaust manifolds 24 upstream of the first and second exhaust purifying devices 32, 33, respectively. The catalyst monitoring exhaust gas sensors 36, 37, are arranged in the exhaust gas feedstream downstream of the first and second exhaust purifying devices 32, 33, respectively. The NOx sensor 40 is arranged in the exhaust gas feedstream downstream of the third exhaust purifying device 38, which may be in an underfloor location. Other exhaust gas sensors may be incorporated, including, e.g., delta pressure sensors, one or multiple temperature sensors, and/or other suitable sensing devices and models for monitoring the exhaust gas feedstream. The first and second engine-out exhaust gas sensors 34, 35, respectively, first and second catalyst monitoring exhaust gas sensors 36, 37 may be wide-range oxygen or lambda sensors having wide-range lambda sensing capability, and in one embodiment are planar-type zirconium oxide dual cell devices each having a sensing element and an integrated electrically-powered heating element.

Such sensors and models may be arranged to monitor or otherwise determine parameters related to the exhaust gas feedstream at specific locations. As such, the aforementioned sensors and/or models may be advantageously employed to monitor performance of individual ones of the exhaust purifying devices, monitor parameters associated with performance of a subset of the exhaust purifying devices, or monitor parameters associated with performance of the overall exhaust aftertreatment system 30.

Engine control includes controlling various engine operating parameters, including controlling engine control states to minimize various exhaust gas constituents through chemical reaction processes that include, by way of non-limiting examples, oxidation, reduction, filtering, and selective reduction. Other engine control states include controlling operating parameters to warm-up the engine 10 and transfer heat or otherwise warm up various ones of the first and second close-coupled catalysts 32, 33 and the third exhaust purifying device 38 to effect efficacious operation thereof.

The term "controller" and related terms such as microcontroller, control, control unit, processor, etc. refer to one or various combinations of Application Specific Integrated Circuit(s) (ASIC), Field-Programmable Gate Array(s) (FPGA), electronic circuit(s), central processing unit(s), e.g., microprocessor(s) and associated non-transitory memory component(s) in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning, buffer circuitry and other components, which may be accessed by and executed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms, and similar terms mean controller-executable instruction sets including calibrations and look-up tables. Each controller executes control routine(s) to provide desired functions.

Routines may be executed at regular intervals, for example every 100 microseconds during ongoing operation. Alternatively, routines may be executed in response to occurrence of a triggering event. Communication between controllers, actuators and/or sensors may be accomplished using a direct wired point-to-point link, a networked communication bus link, a wireless link, or another communication link. Communication includes exchanging data signals, including, for example, electrical signals via a conductive medium; electromagnetic signals via air; optical signals via optical waveguides; etc. The data signals may include discrete, analog and/or digitized analog signals representing inputs from sensors, actuator commands, and communication between controllers.

The term "signal" refers to a physically discernible indicator that conveys information, and may be a suitable waveform (e.g., electrical, optical, magnetic, mechanical or electromagnetic), such as DC, AC, sinusoidal-wave, triangular-wave, square-wave, vibration, and the like, that is capable of traveling through a medium.

The terms "calibration", "calibrated", and related terms refer to a result or a process that correlates a desired parameter and one or multiple perceived or observed parameters for a device or a system. A calibration as described herein may be reduced to a storable parametric table, a plurality of executable equations or another suitable form that may be employed as part of a measurement or control routine.

A parameter is defined as a measurable quantity that represents a physical property of a device or other element that is discernible using one or more sensors and/or a physical model. A parameter may be a discrete value (e.g., either "1" or "0"), a percentage (e.g., 0% to 100%), or an infinitely variable value.

Figure 2:
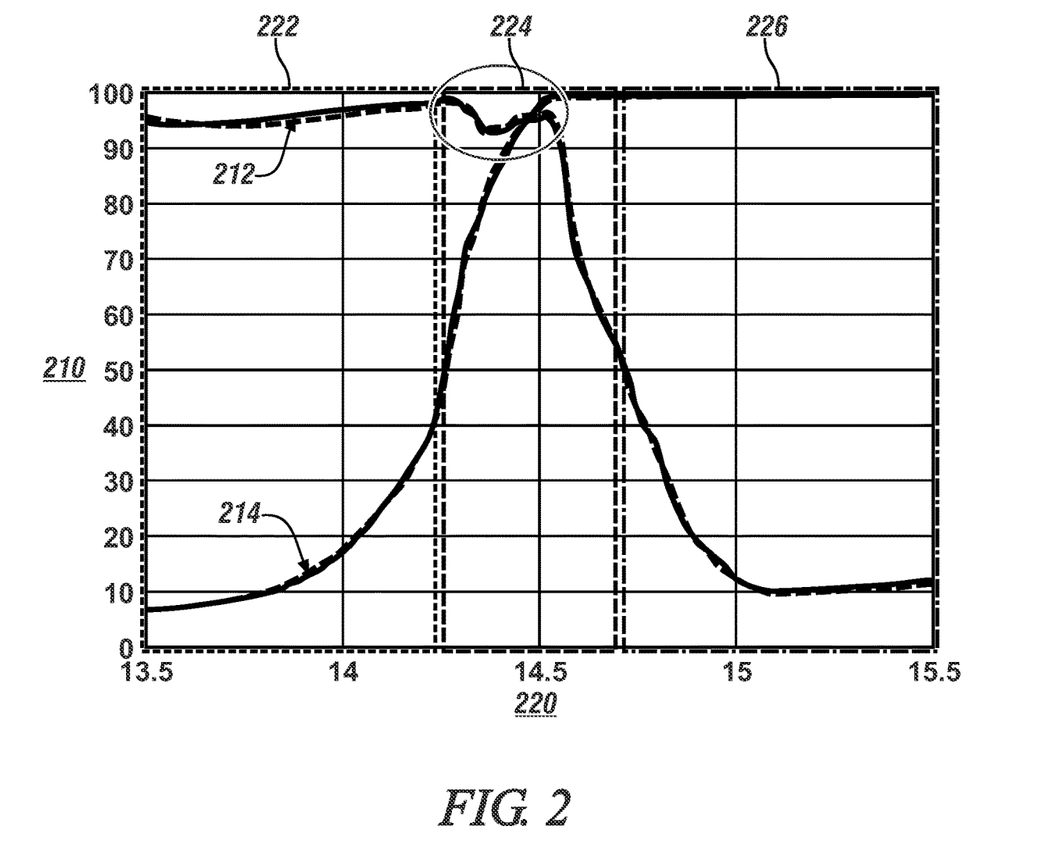
FIG. 2 graphically illustrates NOx and CO conversion efficiencies in relation to air/fuel ratio that are associated with operation of an internal combustion engine and exhaust aftertreatment system, in accordance with the disclosure.

FIG. 2 graphically illustrates NOx and CO conversion efficiencies in relation to air/fuel ratio that are associated with operation of an embodiment of the internal combustion engine 10 and exhaust aftertreatment system 30 that are described with reference to FIG. 1. Conversion efficiency 210 is indicated on the vertical axis, and air/fuel ratio 220 is indicated on the horizontal axis. Line 212 depicts NOx conversion efficiency, and line 214 depicts CO conversion efficiency.

Under engine operating conditions that are rich of stoichiometry, indicated as Zone 1 222, a NOx sensor biased high fault may be most readily detected. Under engine operating conditions that are lean of stoichiometry, indicated as Zone 3 226, a NOx sensor biased low fault may be most readily detected. Under engine operating conditions that are toggling or near stoichiometry, indicated as Zone 2 224, a NOx sensor biased stuck-in-range fault may be most readily detected. This information may be employed in developing diagnostic algorithms for detecting NOx sensor faults, specifically NOx sensor rationality faults, as described with reference to FIG. 3.

Figure 3:
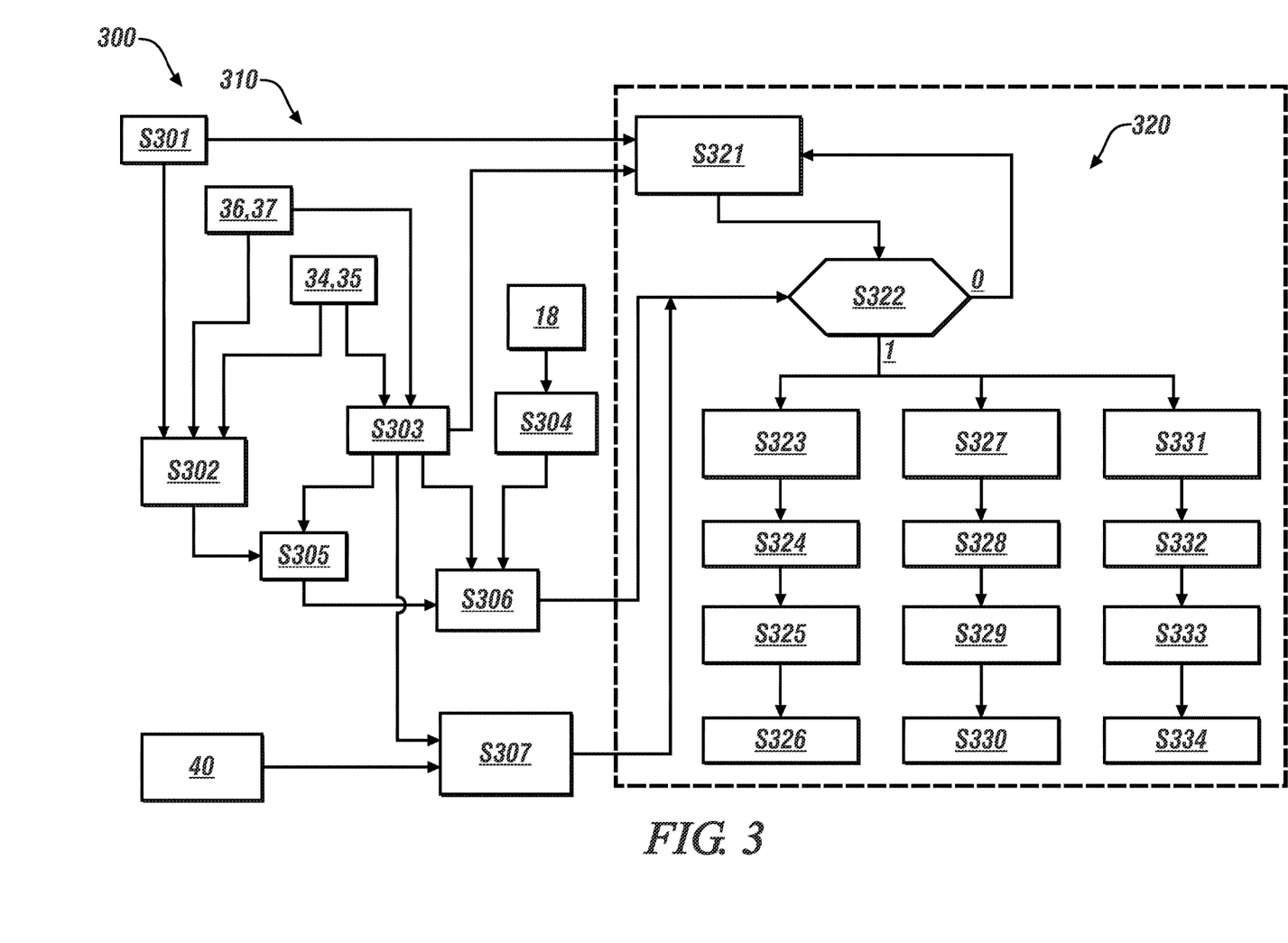
FIG. 3 schematically illustrates a NOx sensor monitoring routine for an embodiment of a NOx sensor that is arranged in an exhaust gas feedstream of an internal combustion engine, in accordance with the disclosure.

FIG. 3 schematically illustrates a sensor monitoring routine 300 is described for monitoring an embodiment of the NOx sensor 40 arranged in an exhaust gas feedstream of the internal combustion engine 10 and located downstream of the exhaust aftertreatment system 30 that are described with reference to FIG. 1. FIG. 3 is represented as a flow chart illustrating an example method of a vehicle computing system receiving instructions from one or more controllers in communication with the system. The vehicle computing system communicating with the one or more modules may be implemented through a computer algorithm, machine executable code, non-transitory computer-readable medium, or software instructions programmed into a suitable programmable logic device(s) of the vehicle, such as the one or more modules, a server in communication with the vehicle computing system, a mobile device communicating with the vehicle computing system and/or server, another controller in the vehicle, or a combination thereof. Although the various steps shown in the flowchart appear to occur in a chronological sequence, at least some of the steps may occur in a different order, and some steps may be performed concurrently or not at all. The teachings may be described herein in terms of functional and/or logical block components and/or various processing steps. Such block components may be composed of hardware, software, and/or firmware components that have been configured to perform the specified functions.

The sensor monitoring routine 300 includes a rationality check to detect a NOx sensor fault that may be in the form of an in-range bias or a stuck-in-range or static output, wherein the diagnostic strategy utilizes a catalyst efficiency model to detect such faults. The sensor monitoring routine 300 includes an entry conditions portion 310 and a monitoring portion 320.

The entry conditions portion 310 includes regularly and periodically monitoring, via the controller 50, signal inputs from various engine and exhaust aftertreatment sensors during operation of the internal combustion engine 10. The engine and exhaust aftertreatment sensors may include, in one embodiment, the first and second engine-out exhaust gas sensors 34, 35, respectively, first and second catalyst monitoring exhaust gas sensors 36, 37, a NOx sensor 40, and engine monitoring sensors, which may include the MAF sensor 18, a crankshaft position sensor, a camshaft position sensor, a coolant temperature sensor, an oil level switch, an oil pressure switch, a throttle position sensor, an EGR flow/position sensor, and an intake air temperature sensor.

The entry conditions portion 310 monitors the signal inputs from various engine and exhaust aftertreatment sensors to determine, via direct monitoring and/or estimation, temperatures of the first, second and third exhaust purifying devices 32, 33, and 38 (S301).

The entry conditions portion 310 monitors the signal inputs from various engine and exhaust aftertreatment sensors to determine, via direct monitoring and/or estimation, oxygen storage capacities of the first, second and third exhaust purifying devices 32, 33, and 38 (S302).

The entry conditions portion 310 monitors the signal inputs from various engine and exhaust aftertreatment sensors to determine, via direct monitoring and/or estimation, an engine-out air/fuel ratio (S303).

The entry conditions portion 310 monitors the signal inputs from various engine and exhaust aftertreatment sensors to determine, via direct monitoring and/or estimation, an exhaust gas feedstream flowrate (S304).

The entry conditions portion 310 determines conversion efficiencies for the first, second and third exhaust purifying devices 32, 33, and 38 based upon the engine-out air/fuel ratio and the respective oxygen storage capacity of the first, second and third exhaust purifying devices 32, 33, and 38 (S305).

The entry conditions portion 310 determines an expected tailpipe NOx concentration in the exhaust gas feedstream downstream of the third exhaust purifying device 38 based upon the conversion efficiencies for the first, second and third exhaust purifying devices 32, 33, and 38 and the exhaust gas feedstream flowrate (S306).

The entry conditions portion 310 subjects the signal output from the NOx sensor 40 to filtering, modelling, and stabilization to determine a sensed NOx concentration (S307).

The steps (S301, . . . , S307) of the entry conditions portion 310 are periodically performed and executed to provide information to the monitoring portion 320.

The monitoring portion 320 includes evaluating various operating conditions as entry conditions to determine whether the operating conditions enable reliable execution of fault detection strategies for the NOx sensor 40 (S321). The entry conditions include, but are not limited to, the temperatures of the first, second and third exhaust purifying devices 32, 33, and 38 (S301), the engine-out air/fuel ratio (S303), and the exhaust gas feedstream flowrate (S304).

The criteria to enable execution of the monitoring portion include achieving an exhaust volume flow and catalyst/exhaust temperature at which the expected tailpipe NOx concentration is stable, coupled with catalyst or exhaust temperature being in a range that ensures catalyst light off has occurred, and a minimum exhaust volume flow to ensure accurate NOx concentration reading by the NOx sensor and accurate NOx concentration estimation by the NOx concentration model Execution of the monitoring portion 320 may proceed as follows. The steps may be executed in a suitable order, and are not limited to the order described with reference to FIG. 3. As employed herein, the term "1" indicates an answer in the affirmative, or "YES", and the term "0" indicates an answer in the negative, or "NO".

The parameters for the entry conditions are evaluated to ensure that the monitoring portion 320 executes at exhaust volume flow levels and catalyst/exhaust temperatures at which an expected tailpipe NOx concentration is stable, at catalyst and exhaust temperatures that ensure the catalyst is lit off and has sufficient conversion efficiency, and at a minimum exhaust volumetric flowrate to ensure accurate NOx concentration reading by the NOx sensor and accurate NOx concentration estimation by the NOx concentration model.

When the entry conditions are met or exceeded, the sensed tailpipe NOx concentration (determined at S307) is compared to the expected tailpipe NOx concentration in the exhaust gas feedstream downstream of the third exhaust purifying device 38 (determined at S306) (S322). The catalyst oxygen storage capacity (OSC) and catalyst efficiency model employ pre- and post-O2 sensor values and catalyst temperature to calculate oxygen storage and modeled catalyst efficiency. The modeled catalyst efficiency can be used to determine the expected NOx concentration. The tailpipe NOx sensor measures the NOx concentration in the exhaust, which is compared to the expected NOx concentration to determine if the sensor reading is biased high or low or is stuck in range.

When an absolute difference between the expected tailpipe NOx concentration and the sensed NOx concentration is less than a threshold value (S322)(0), no further action is taken, and the routine cycles back to the entry conditions step (S321).

When the absolute difference between the expected tailpipe NOx concentration and the sensed NOx concentration is greater than the threshold value (S322)(1), the routine evaluates the exhaust gas air/fuel ratio and acts as follows.

When the engine-out air/fuel ratio is stoichiometric or rich (S323), the fault is subjected to debouncing delays and filtering (S324), and the absolute difference between the expected tailpipe NOx concentration and the sensed NOx concentration is subjected to an exponentially weighted moving average (EWMA) analysis (S325). The output of the EWMA analysis is evaluated and reported out as an active fault associated with a biased-high sensor offset fault (S326). During stoichiometric to slightly rich of stoichiometric operation, NOx catalyst efficiency is expected to be high resulting in a low NOx concentration. A biased high NOx sensor fault can be detected under these operating conditions.

When the engine-out air/fuel ratio is lean (S327), the fault is subjected to debouncing delays and filtering (S328), and the absolute difference between the expected tailpipe NOx concentration and the sensed NOx concentration is subjected to an exponentially weighted moving average (EWMA) analysis (S329). The output of the EWMA analysis is evaluated and reported out as an active fault associated with a biased-low sensor offset fault (S330). During lean of stoichiometric operation, NOx catalyst efficiency is expected to be low resulting in a high NOx concentration. A biased low NOx sensor fault can be detected under these operating conditions.

When the engine-out air/fuel ratio is transitioning between rich and lean (S331), the fault is subjected to debouncing delays and filtering (S332), and the absolute difference between the expected tailpipe NOx concentration and the sensed NOx concentration is subjected to an exponentially weighted moving average (EWMA) analysis (S333). The output of the EWMA analysis is evaluated and reported out as an active fault associated with a stuck-in-range sensor fault (S334). During transitions from stoichiometric or slightly rich of stoichiometric to lean of stoichiometric operation, the NOx catalyst efficiency is expected to transition from high to low resulting in an expected transition of NOx concentration from low to high. A static in-range NOx sensor fault can be detected under these transient operating conditions.

The monitors described are expected to detect sensor bias faults that are outside the expected NOx sensor system measurement tolerance capability.

Embodiments in accordance with the present disclosure may be embodied as an apparatus, method, or computer program product. Accordingly, the present disclosure may take the form of an entirely hardware embodiment, an entirely software embodiment (including firmware, resident software, micro-code, etc.), or an embodiment combining software and hardware aspects that may generally be referred to herein as a "module" or "system." Furthermore, the present disclosure may take the form of a computer program product embodied in a tangible medium of expression having computer-usable program code embodied in the medium.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the claims.

What is claimed is:

1. A method for monitoring a NOx sensor arranged in an exhaust gas feedstream of an internal combustion engine downstream of an exhaust aftertreatment system, the method comprising:
    determining, via a controller, a temperature of an exhaust purifying device of the exhaust aftertreatment system;
    determining an exhaust gas flowrate;

determining an air/fuel ratio of the exhaust gas feedstream;
determining an oxygen storage capacity of the exhaust purifying device based upon the temperature of the exhaust purifying device;
determining an efficiency of the exhaust purifying device based upon the oxygen storage capacity;
determining, via the controller, an expected NOx concentration in the exhaust gas feedstream based upon the air/fuel ratio of the exhaust gas feedstream, the efficiency of the exhaust purifying device, and the exhaust gas flowrate;
determining a measured NOx concentration in the exhaust gas feedstream based upon a signal input from the NOx sensor;
comparing, via the controller, the measured NOx concentration in the exhaust gas feedstream and the expected NOx concentration in the exhaust gas feedstream;
detecting an in-range fault related to the NOx sensor based thereon, including detecting a biased-high sensor offset fault when the air/fuel ratio is stoichiometric or rich and an absolute difference between the measured NOx concentration in the exhaust gas feedstream and the expected NOx concentration in the exhaust gas feedstream is greater than a threshold; and
controlling the internal combustion engine in response to the in-range fault.

2. The method of claim 1, further comprising detecting a biased-low sensor offset fault when the air/fuel ratio is lean and the absolute difference between the measured NOx concentration in the exhaust gas feedstream and the expected NOx concentration in the exhaust gas feedstream is greater than the threshold.

3. The method of claim 1, further comprising detecting a stuck-in-range sensor fault when the air/fuel ratio is transitioning between a lean air/fuel ratio and a rich air/fuel ratio and the absolute difference between the measured NOx concentration in the exhaust gas feedstream and the expected NOx concentration in the exhaust gas feedstream is greater than the threshold.

4. The method of claim 1, comprising comparing the measured NOx concentration in the exhaust gas feedstream and the expected NOx concentration in the exhaust gas feedstream only when the temperature of the exhaust purifying device indicates the exhaust purifying device has achieved a light-off state.

5. The method of claim 1, comprising comparing the measured NOx concentration in the exhaust gas feedstream and the expected NOx concentration in the exhaust gas feedstream only when the exhaust gas flowrate and the air/fuel ratio of the exhaust gas feedstream determine the expected NOx concentration in the exhaust gas feedstream is accurate.

6. A method for monitoring a NOx sensor arranged in an exhaust gas feedstream of an internal combustion engine and downstream of an exhaust purifying device, the method comprising:
determining, via a controller, an expected NOx concentration in the exhaust gas feedstream;
determining a measured NOx concentration in the exhaust gas feedstream based upon a signal input from the NOx sensor;
determining an air/fuel ratio of the exhaust gas feedstream;
comparing, via the controller, the measured NOx concentration in the exhaust gas feedstream and the expected NOx concentration in the exhaust gas feedstream;
detecting an in-range fault including a biased-low sensor offset fault when an air/fuel ratio is lean and an absolute difference between the measured NOx concentration in the exhaust gas feedstream and the expected NOx concentration in the exhaust gas feedstream is greater than a threshold; and
controlling the internal combustion engine in response to the in-range fault.

7. The method of claim 6, comprising:
determining a temperature of the exhaust purifying device;
monitoring, via an upstream exhaust gas sensor and a downstream exhaust gas sensor, the exhaust purifying device;
determining an oxygen storage capacity of the exhaust purifying device based upon the temperature of the exhaust purifying device and the monitoring of the exhaust purifying device via the upstream exhaust gas sensor and the downstream exhaust gas sensor;
determining an efficiency of the exhaust purifying device based upon the oxygen storage capacity;
determining an exhaust gas flowrate; and
determining the expected NOx concentration in the exhaust gas feedstream based upon the air/fuel ratio of the exhaust gas feedstream, the efficiency of the exhaust purifying device, and the exhaust gas flowrate.

8. The method of claim 6, further comprising detecting a biased-high sensor offset fault when the absolute difference between the measured NOx concentration in the exhaust gas feedstream and the expected NOx concentration in the exhaust gas feedstream is greater than the threshold and an air/fuel ratio is stoichiometric or rich of stoichiometry.

9. The method of claim 6, further comprising detecting a stuck-in-range sensor fault when the air/fuel ratio is transitioning between a lean air/fuel ratio and a rich air/fuel ratio and the absolute difference between the measured NOx concentration in the exhaust gas feedstream and the expected NOx concentration in the exhaust gas feedstream is greater than the threshold.

10. The method of claim 6, comprising comparing the measured NOx concentration in the exhaust gas feedstream and the expected NOx concentration in the exhaust gas feedstream only when the temperature of the exhaust purifying device indicates the exhaust purifying device has achieved a light-off state.

11. The method of claim 6, comprising comparing the measured NOx concentration in the exhaust gas feedstream and the expected NOx concentration in the exhaust gas feedstream only when the exhaust gas flowrate and the air/fuel ratio of the exhaust gas feedstream determine the expected NOx concentration in the exhaust gas feedstream is accurate.

12. A system for monitoring a NOx sensor arranged in an exhaust gas feedstream of an internal combustion engine and downstream of an exhaust purifying device, the system comprising:
a mass airflow sensor;
a first exhaust gas sensor arranged upstream of the exhaust purifying device;
a second exhaust gas sensor arranged downstream of the exhaust purifying device;
a controller, in communication with the mass airflow sensor and the first and second exhaust gas sensors; the controller including algorithmic code that is executable to:
determine a temperature of the exhaust purifying device, determine an exhaust gas flowrate,
determine an air/fuel ratio of the exhaust gas feedstream,
determine an oxygen storage capacity of the exhaust purifying device based upon the temperature of the exhaust purifying device;
determine an efficiency of the exhaust purifying device based upon the oxygen storage capacity;
determine an expected NOx concentration in the exhaust gas feedstream based upon the air/fuel ratio of the exhaust gas feedstream, the efficiency of the exhaust purifying device, and the exhaust gas flowrate;
determine a measured NOx concentration in the exhaust gas feedstream based upon the NOx sensor;
compare the measured NOx concentration in the exhaust gas feedstream and the expected NOx concentration in the exhaust gas feedstream; and
 detect, via the controller, a stuck-in-range sensor fault when the air/fuel ratio is transitioning between a lean air/fuel ratio and a rich air/fuel ratio and an absolute difference between the measured NOx concentration in the exhaust gas feedstream and the expected NOx concentration in the exhaust gas feedstream is greater than a threshold.

13. The system of claim 12, further comprising the instruction set being executable to detect a biased-high sensor offset fault when the absolute difference between the measured NOx concentration in the exhaust gas feedstream and the expected NOx concentration in the exhaust gas feedstream is greater than the threshold and an air/fuel ratio is stoichiometric or rich of stoichiometry.

14. The system of claim 12, further comprising the instruction set being executable to detect a biased-low sensor offset fault when the air/fuel ratio is lean and the absolute difference between the measured NOx concentration in the exhaust gas feedstream and the expected NOx concentration in the exhaust gas feedstream is greater than the threshold.

15. The system of claim 12, comprising the instruction set being executable to compare the measured NOx concentration in the exhaust gas feedstream and the expected NOx concentration in the exhaust gas feedstream only when the temperature of the exhaust purifying device indicates the exhaust purifying device has achieved a light-off state.

* * * * *